United States Patent
Li

(10) Patent No.: US 9,585,944 B2
(45) Date of Patent: Mar. 7, 2017

(54) APPLICATION OF PRDX2 AND/OR PRDX6 IN IMPROVING SPERM QUALITY OR TREATING MALE INFERTILITY

(75) Inventor: Jianyuan Li, Shandong (CN)

(73) Assignee: Yantai Ju Jie Bioengineering Limited Company, Yantai, Shandong (CN)

( * ) Notice: Subject to any disclaimer, the term of this patent is extended or adjusted under 35 U.S.C. 154(b) by 0 days.

(21) Appl. No.: 14/119,978

(22) PCT Filed: May 23, 2012

(86) PCT No.: PCT/CN2012/075966
§ 371 (c)(1),
(2), (4) Date: Jan. 16, 2014

(87) PCT Pub. No.: WO2012/159569
PCT Pub. Date: Nov. 29, 2012

(65) Prior Publication Data
US 2014/0147430 A1   May 29, 2014

(30) Foreign Application Priority Data
May 24, 2011 (CN) .......................... 2011 1 0136707

(51) Int. Cl.
*A61K 38/44* (2006.01)

(52) U.S. Cl.
CPC ....... *A61K 38/44* (2013.01); *C12Y 111/01015* (2013.01)

(58) Field of Classification Search
None
See application file for complete search history.

(56) References Cited

FOREIGN PATENT DOCUMENTS

| CN | 102485272 | 6/2012 |
|---|---|---|
| EP | 1566182 | 8/2005 |
| WO | 2006083090 | 8/2006 |
| WO | 2010101301 | 9/2010 |
| WO | WO2010101301 | * 9/2010 |
| WO | 2012/075911 | 6/2012 |

OTHER PUBLICATIONS

Accession P30041. Apr. 1, 1993.*
Accession P32119. Oct. 1, 1993.*
Kumar et al. Indian Journal of Biochemistry & Biophysics. vol. 46, Apr. 2009, pp. 172-177.*
Chica et al. Curr Opin Biotechnol. Aug. 2005;16(4):378-84.*
Sen et al. Appl Biochem Biotechnol. Dec. 2007;143(3):212-23.*
"Peroxiredoxin", Chinese Journal of Andrology, vol. 24, No. 8, pp. 70-72, 2010.
International Search Report for PCT/CN2012/075966 dated Aug. 30, 2012, 10 pages.
Ying-Hao Han et al., "Inhibitory role of peroxiredoxin II (Prx II) on cellular senescence," FEBS Letters, vol. 579 (2005), p. 4897-4902.
JianYuan Li et al., "Systematic Mapping and Functional Analysis of a Family of Human Epididymal Secretory SpermLocated Proteins," Molecular & Cellular Proteomics, vol. 9, No. 11 (2010), p. 2517-2528.
Rajkumar Tulsawani et al., "Neuroprotective effect of peroxiredoxin 6 against hypoxia-induced retinal ganglion cell damage," BMC Neuroscience, vol. 11, No. 125 (2010), 14 pages.
Wen Zhao et al., "Protection of peroxiredoxin II on oxidative stress-induced cardiomyocyte death and apoptosis," Basic Research in Cardiology, vol. 104, No. 4 (2009), p. 377-389.
Wen-jiang Zheng et al., "Analysis of the expression and antioxidative property of a peroxiredoxin 6 from Scophthalmus maximus," Fish & Shellfish Immunology, vol. 29 (2010), p. 305-311.
Official Communication issued for European patent application No. 12790325.0, dated Sep. 25, 2015 (6 pages).

* cited by examiner

*Primary Examiner* — Christian Fronda
(74) *Attorney, Agent, or Firm* — Hamre, Schumann, Mueller & Larson, P.C.

(57) ABSTRACT

Provided in the present invention is an application for PRDX2 and/or PRDX6 in the preparation of a pharmaceutical composition to treat or prevent damage, aging or diseases resulting from an increase in reactive oxygen species (ROS).

10 Claims, 3 Drawing Sheets

APPLICATION OF PRDX2 AND/OR PRDX6 IN IMPROVING SPERM QUALITY OR TREATING MALE INFERTILITY

FIELD OF THE INVENTION

The present invention relates to the field of biotechnology and medicine and, in particular, to a novel usage of PRDX2 and/or PRDX6. More specifically, it relates to use of PRDX2 and/or PRDX6 in treatment or prevention of diseases, aging or injuries caused by ROS increases.

BACKGROUND OF INVENTION

When using oxygen, cells produce free radicals, e.g., reactive oxygen species (ROS) and reactive nitrogen species (RNS). In our bodies, each cell produces $2.5 \times 10^{11}$ ROS molecules per day, and human body can produce $40 \times 10^{21}$ ROS per day. ROS not only provides and delivers life-sustaining energy, but also helps human body to eliminate bacteria and pathogens, toxins and "junks". ROS also serve as an initiator and adjuster for various metabolisms and signal channels inside our bodies such as JNK/SAPK, P38MAPK, IKK/NF-KB, P13K, Akt, CD40/CD40L, PKC, etc, activates and regulates various transcription factors (e.g. AP-1, Nrf2, NF-KB, p53, ATF-1, HIF, HSP, SIFT-1, MST/FOXO, etc.), influences in vivo transcription and expression of various genes and participates in inflammation, immunization, reproduction, development, metabolism, cell growth, proliferation, cell regeneration, repair, and other modulations in important life processes. ROS enhances and maintains metabolism in cell, tissue and body, thereby maintaining and ensuring normal life activities.

Free radicals in human body are generated in two aspects. Firstly, they are generated from the various metabolic reactions in human body. Secondly, they arise from the exogenous free radical generated from splitting of covalent bonds resulted from high temperature, radiation, photolysis, chemical substances in the environment, such as smoking, drinking alcohol, pollution, drugs, diseases etc.

We have, inside our bodies, a dynamic antioxidant system involving, e.g. superoxide dismutase (SOD), catalase (CAT), glutathione peroxidase (GSH-Px), which can timely and rapidly remove the excessive ROS inside the body. Under normal physiological conditions, the oxidative-antioxidant system inside our bodies maintains a homeostasis, thereby ensuring normal oxidative stress reactions and preventing ROS from damaging human bodies. Only when ROS is excessively generated and expression of antioxidant enzymes is in shortage, the balance between oxidation and antioxidation is lost and ROS is unable to be cleared timely, and cumulates in the body, thereby resulting in cellular and tissue damages (i.e., oxidative stress) and risk of human health.

ROS can directly or indirectly oxidize or damage DNA, proteins and lipids. ROS can induce gene mutation, denaturation of proteins and peroxidation of lipids, which are considered as major risk factors leading to human aging and various significant diseases, such as infertility, cataract, cancers, cardiovascular diseases, senile dementia/neurodegenerative diseases (such as Alzheimer's disease, Parkinson's disease), diabetes, inflammations (such as osteoarthritis, rheumatoid arthritis, bronchitis, etc.), infections, myocardial ischemia-reperfusion injuries, organ transplantations, atherosclerosis, etc.

Nowadays there are many "drugs for antioxidation". However, there are few drugs that are genuinely effective in regulating oxidation-antioxidation balance.

SUMMARY OF THE INVENTION

One objective of the present invention is to provide a new use of PRDX2 protein and/or PRDX6 protein in treating or preventing injury, aging or diseases because of increase of reactive oxygen species (ROS).

Another objective of the present invention is to provide a composition, including a pharmaceutical composition and cosmetic composition, which comprises PRDX2 protein and/or PRDX6 protein as an active ingredient.

The present invention is further intended to provide a method for ameliorating sperm quality or cure asthenospermia-induced male infertilities.

In the first aspect of the present invention, it provides a use of a peroxide oxidoreductase in preparation of pharmaceutical composition for treatment or prevention of damage, aging or diseases resulting from an increase of reactive oxygen species (ROS), wherein the peroxide oxidoreductase comprises PRDX2 protein and/or PRDX6 protein.

In a preferred embodiment, the damage, aging or diseases resulting from ROS increase comprise one or more type selected from the group consisting of (1) Damages, aging or diseases resulting from ROS increase caused by irradiation or radiation;

(2) Damages, aging or diseases resulting from ROS increase caused by hyperglycemia (such as diabetes);

(3) Various smoking-induced tissue damage;

(4) Various tissue damages caused by drinking alcohol;

(5) Other diseases induced by ROS increase, wherein the disease is selected from the group consisting of atherosclerosis, hypertension, cancer, osteoarthritis, rheumatic arthritis, pulmonary fibrosis, epilepsy or neurodegenerative diseases (e.g. Alzheimer's disease, Parkinson's disease);

(6) Damages resulting from cell cryopreservation-recovery process;

(7) Ischemia reperfusion injury;

(8) Aseptic necrosis of caput femoris, or bedsore;

(9) Injuries or diseases caused by ROS increase because of administration of medicament e.g. chemotherapy medicament or organophosphorus pesticides;

(10) Dermal issues (e.g. wrinkles, marks and burns, etc.);

(11) Diabetic complication (e.g. pedopathy (gangrene), eye disease, kidney disease, encephalopathy, etc.).

In a preferred embodiment, the pharmaceutical composition is used as (1) a cell protective agent, organ protective agent, or tissue protective agent;

(2) a medicament for improving sperm quality in asthenospermia patient or treatment of male infertility; and in a preferred embodiment, the sperm is in mature stage;

(3) a medicine or cosmetic for anti-aging, scar-repairing, anti-wrinkle, wrinkle-removing, freckle-lightening, whitening, sun screening, or prevention of skin cancer;

(4) a medicine for treatment of burn, scald or corneal injury;

(5) a medicine for accelerating heal process of wounds (such as cuts, vulnera, etc.); or (6) a medical or healthcare product for protecting tissues or cells from oxidative damages or for antioxidation.

In a preferred embodiment, the protective agent is a cryoprotectant agent.

In a preferred embodiment, the protective agent is used for preparation of cell preservation fluid, organ preservation fluid, or tissue preservation fluid, and preferably for preparation of organ transplant preservation fluid.

In a preferred embodiment, the cell is an animal cell (preferably, a mammalian cell, such as a human cell), wherein the cell comprises sperm, egg, or various tissue cells.

In a preferred embodiment, the tissue comprises various organs or tissues of animal, preferably a mammal such as human.

In a preferred embodiment, the PRDX2 protein comprises mammalian PRDX2 protein or active fragments or derivatives thereof; and PRDX6 proteins comprises mammalian PRDX6 protein or active fragments or derivatives thereof.

In a preferred embodiment, the PRDX2 protein comprises human PRDX2 protein or active fragments or derivatives thereof; and PRDX6 protein comprises human PRDX6 protein or active fragments or derivatives thereof.

In a preferred embodiment, the PRDX2 protein or PRDX6 protein is recombinant.

In a preferred embodiment, the PRDX2 protein comprises a protein whose amino acid sequence is shown in SEQ ID NO: 4 or a fragment as shown in position 6 to 164 of SEQ ID NO: 4, or a fusion protein thereof formed with an expression tag.

The PRDX6 protein comprises a protein whose amino acid sequence is shown in SEQ ID NO: 2 or a fragment as shown in position 5 to 169 of SEQ ID NO: 2, or a fusion protein thereof formed with an expression tag.

In the second aspect of the present invention, it provides a composition comprising (a) PRDX2 protein and/or PRDX6 protein; and (b) a pharmaceutically, cosmetically or alimentarily acceptable carrier.

In a preferred embodiment, the PRDX2 protein comprises mammalian PRDX2 protein or active fragments or derivatives thereof; and PRDX6 proteins comprises mammalian PRDX6 protein or active fragments or derivatives thereof.

In a preferred embodiment, the PRDX2 protein comprises human PRDX2 protein or active fragments or derivatives thereof; and PRDX6 protein comprises human PRDX6 protein or active fragments or derivatives thereof.

In a preferred embodiment, the PRDX2 protein or PRDX6 protein is recombinant.

In a preferred embodiment, the composition is a pharmaceutical composition, food composition, healthcare or supplemental composition, or cosmetic composition.

In a preferred embodiment, the composition is in dosage of injection, liniment, spray, emulsion, cream, paste (including ointment), gel, drop, patch or mask.

In a preferred embodiment, the cosmetic comprises a orally administered cosmetic (such as a cosmetic against oral inflammation), spray, lotion, lipbalm, sunscreen, day cream, night cream, toner, or mask.

In the third aspect of the present invention, it provides a method for treatment or prevention of damage, aging or diseases resulting from ROS increase, comprising the following steps: administrating (i) PRDX2 protein and/or PRDX6 protein, or (ii) the composition according to the second aspect of the present invention, to a subject in need of treatment or prevention.

In a preferred embodiment, the method has one or more of the following effects:
 (i) improving sperm quality of asthenospermia patient;
 (ii) anti aging, scar-repairing, anti-wrinkle, wrinkle-erasing, freckle-lightening, whitening, sunburn-preventing, or skin cancer-preventing effect;
 (iii) treating burn or scald or corneal injury;
 (iv) accelerating healing of wounds (e.g. cuts, vulnera, etc.);
 (v) protecting tissues or cells from oxidative damages;
 (vi) treating or preventing complication of diabetes, such as pedopathy (gangrene), eye disease, kidney disease, encephalopathy, etc.

In a preferred embodiment, the method has the following effect(s):
 (1) increasing impregnation rate of asthenospermia patient; or
 (2) protecting mature sperm cells.

In a preferred embodiment, the method further possesses one or more of the following effects:
 (1) relieving asthenopia, enhancing and improving vision or preventing progressive vision loss;
 (2) resisting light injuries and lipid peroxidation damages, increasing cellular potential for scavenging oxygen radicals, lowering hue differences, treating myopia, amblyopia, presbyopia, glaucoma, or floaters;
 (3) inhibiting free radical generation in the vitreous, accelerating clearance and excretion of free radicals, preventing glycation and oxidation of proteins in the vitreous body, protecting SH groups of soluble proteins from damages, restoring insoluble proteins into soluble proteins, preventing phacoscotasmus (lens opacity), or treating or preventing formation and development of progressive cataracts;
 (4) treating senile cataract, diabetic cataract, traumatic cataract, radiation cataract, after-cataract, or treating phacoscotasmus in immature stage, expansion stage and mature stage.

In a preferred embodiment, the oxidative damage includes one or more of the following damages:
 (1) damages caused by radiotherapy or chemotherapy;
 (2) damages caused by smoking or drinking;
 (3) ischemia reperfusion damages;
 (4) damage caused by hyperglycemia from diabetes.

In the fourth aspect of the present invention, it provides a method for improving sperm quality or treatment of male infertility, which comprises administrating (i) PRDX2 protein and/or PRDX6 protein, or (ii) the composition according to the second aspect of the present invention to an asthenospermia patient.

In the fifth aspect of the present invention, it provides a method for preparing the composition in the second aspect of the present invention, comprising mixing the PRDX2 protein and/or PRDX6 protein with a pharmaceutically, cosmetically or alimentarily acceptable carrier or excipient, thereby forming the composition in the second aspect of the present invention.

In the sixth aspect of the present invention, it provides a use of Prx-6 protein in preparing a medicine for treating corneal injury.

In a preferred embodiment, the Prx-6 protein is human Prx-6 protein.

In a preferred embodiment, the Prx-6 protein is recombinant.

In a preferred embodiment, the Prx-6 protein comprises a protein whose amino acid sequence is shown in SEQ ID NO: 2, or a fusion protein thereof formed with an expression tag.

In the seventh aspect of the present invention, it provides a pharmaceutical composition for treatment of corneal injury, wherein the pharmaceutical composition comprises Prx-6 protein and a pharmaceutically acceptable carrier, and the pharmaceutical composition is an ophthalmic preparation.

In a preferred embodiment, the Prx-6 protein is human Prx-6 protein.

In a preferred embodiment, the Prx-6 protein is recombinant protein.

In a preferred embodiment, the ophthalmic preparation is an eye drop, an ophthalmic gel or an ophthalmic ointment.

In the eighth aspect of the present invention, it provides a method for the treatment of corneal injury, comprising the following steps: dripping or applying Prx-6 protein or the pharmaceutical composition in the seventh aspect of the present invention into the conjunctival sac of a subject in need of treatment.

In a preferred embodiment, the treatment comprises inhibiting corneal neovascularization, repairing damaged corneal epithelial cells, relieving corneal edema, recovering corneal opacity and vision, scavenging antioxidant radicals and accelerating recovery of diseased inflammatory tissues.

From the preliminary cell experiments to animal experiments, the inventor has proved that the PRDX proteins play a major role in scavenging reactive oxygen and adjusting reactive oxygen-dependent signal transduction. PRDX protein is a highly promising and effective antioxidant which, as a medical ingredient, is effective for treating and preventing diseases or adverse changes caused by ROS increase.

It should be understood that, in the present invention, each of the technical features specifically described above and below (such as those in the Examples) can be combined with each other, thereby constituting a new or preferred technical solutions which need not be specified again herein.

DESCRIPTION OF FIGURES OF THE INVENTION

FIG. 1 shows the PCR amplification of Prx-6 gene. Lane 1: control; Lane 2: Prx-6; M: Marker.

FIG. 2 shows affinity purification chromatography of Prx-6 protein. Peak 1: protein impurity; peak 2: Prx-6 protein.

FIG. 3 shows the purification profile of PRDX6 protein by 12% SDS-PAGE. Lane 1: Marker (Fermentas); lane 2: PRDX6 protein purified by affinity chromatography and desalination; lane 3: peak 1; lane 4: flow-through protein from sample; lane 5: supernatant of bacteria lysate (i.e. the loaded sample).

In each of the aforesaid figures, any two groups possessing a same letter have no significant differences in statistic analysis. For instance, there is no significant difference between group A and group AB. Any two groups without any common letter have a significant difference in statistic analysis. For instance, there is a significant difference between group A and group B, or between group A and group D.

Figure 7:
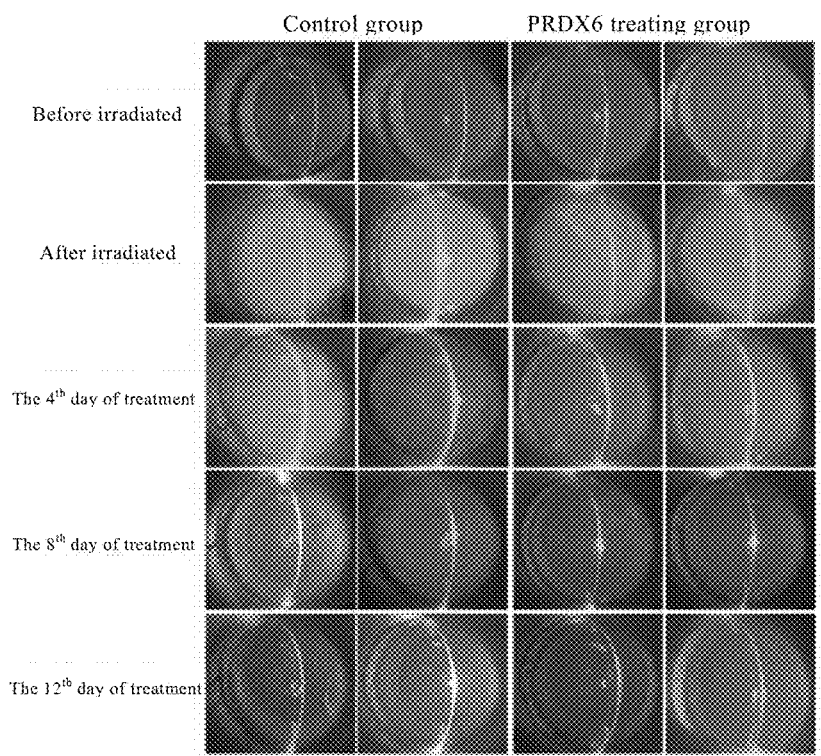

FIG. 7 shows observation results of recombinant Prx-6 protein in treatment of rat's corneal injuries under slit lamp microscope. Images from left to right: control group (2 rats); and Prx-6 group (2 rats). Images from top to bottom: before UV irradiation; after UV irradiation; 4 days in treatment; 8 days in treatment; 12 days in treatment.

DETAILED DESCRIPTION OF THE INVENTION

Through comprehensive and intensive research, the inventor has unexpectedly discovered that PRDX6 protein and PRDX2 protein can be used to prepare a pharmaceutical composition for treating or preventing diseases caused by ROS increase. The medicine containing PRDX6 protein and/or PRDX2 protein as active ingredients can not only be used to protect cells such as HEF, but also be used for treating or preventing various diseases caused by ROS increase, or relieving symptoms caused by ROS increase. The present invention is accomplished based on the discovery.

PRDX6 Protein

As used herein, the terms "PRDX6 protein", "Prx-6 protein", "HEL-S-128m" can be used interchangeably and all refer to a protein or polypeptide having an amino acid sequence of human PRDX6. They may or may not contain the starting methionine. It should be understood that these terms cover both human (sourced) proteins, and homologs or homologous proteins in other mammals (such as dogs, cattle, sheep, monkeys, rodents (e.g., mice)) having same functions. In addition, the terms cover a wild-type or mutant PRDX6 protein.

The GenBank accession number of cDNA sequence of human PRDX6 gene is NM_004905.2, as shown in SEQ ID NO: 1. The GenBank accession number of amino acid sequence of human PRDX6 protein is NP_004896.1, as shown in SEQ ID NO: 2.

It should be understood that since the nucleotide sequence and amino acid sequences of PRDX6 are known, the protein thereof can be obtained by common recombinant DNA technology in the field.

A particularly preferred protein is analogues of PRDX6 protein, i.e. PRDX6 homologous proteins in other mammals (such as cattle, sheep, rabbits, dogs, monkeys, rats, etc.). The coding sequences of homologous proteins in other species can be obtained by using hybridization or amplification methods according to the sequence of PRDX6. Then the homologous proteins can be obtained by using conventional recombinant methods.

Proteins of the present invention can be recombinant polypeptide, natural polypeptide, synthetic polypeptide, and preferably recombinant polypeptide. According to the host used in the recombinant production protocol, the polypeptides of the present invention can be glycosylated or non-glycosylated. Polypeptides of the invention may or may not include an initial methionine residue.

The invention also includes active fragments of human PRDX6 protein, derivatives and analogs thereof. As used herein, "active fragment", "derivative" and "analog" refer to a polypeptide that substantially retains the same biological function or bio-activity of the natural human protein PRDX6 of the present invention. The active fragment, derivative and analog herein may be (i) polypeptide with one or more conservative or non-conservative amino acid residue(s) (preferably conservative amino acid residue(s)) substituted, wherein such substituted amino acid residue may or may not be coded by the genetic code, or (ii) polypeptide with a substituent group in one or more amino acid residues, or (iii) polypeptide formed from the fusion of mature polypeptide and another compound (such as compounds that prolong half-life periods of polypeptides, e.g. polyethylene glycol), or (iv) the polypeptide which is formed by fusion of additional amino acid sequence to said polypeptide sequence (such as a leader sequence or secretory sequence or a sequence used for purification thereof or a proteinogen sequence, or a fusion protein formed thereof with antigen IgG fragments). According to the teachings herein, these fragments, derivatives and analogs are within the knowledge of the skilled in the art.

In the present invention, "human PRDX6 polypeptide" refers to a polypeptide having the sequence of SEQ ID NO: 2 and human PRDX6 activity. It also includes the variations of SEQ ID NO: 2 which has as the same function of human PRDX6. Those variations include (but not limited to) deletion, insertion and/or substitution of several (usually 1-50, preferably 1-30, more preferably 1-20, most preferably 1-10) amino acids, and addition of one or more (usually 20 or less, preferably 10 or less, more preferably 5 or less) amino acids on the C-terminus and/or N-terminus. For example, in the present field, the function of protein won't be changed when it is substituted by amino acids of approximate or similar properties. Again for example, in the present field, the function of protein won't be changed when one or several amino acids are added on the C-terminus and/or N-terminus. It also includes active fragments or active derivatives of human PRDX6 protein. A preferred active fragment is a polypeptide whose amino acid sequence is shown in position 5 to 169 in SEQ ID NO: 2.

PRDX2 Protein

As used herein, the terms "PRDX2 protein", "Prx-2 protein", "HEL-S-2a" can be used interchangeably and all refer to a protein or polypeptide having the amino acid sequence of human PRDX2. They may or may not contain the starting methionine. It should be understood that these terms include both human (source) proteins, and homologs or homologues proteins in other mammals (such as dogs, cattle, sheep, monkey, rodent (e.g., mouse)) having same functions. Furthermore, the terms include a wild-type and mutant PRDX2 protein.

The GenBank accession number of cDNA sequence of human PRDX2 gene is NM_005809.4, as shown in SEQ ID NO: 3. The GenBank accession number of amino acid sequence of human PRDX2 protein is NP_005800.3, as shown in SEQ ID NO: 4.

It should be understood that since the nucleotide sequence and the amino acid sequence of PRDX2 are known, the protein thereof could be obtained by common recombinant DNA technology in the field.

A particularly preferred protein is analogues of PRDX2 protein, i.e. PRDX2 homologous proteins in other mammals (such as cattle, sheep, rabbits, dogs, monkeys, rats, etc.). The coding sequences of homologous proteins in other species can be obtained by using hybridization or amplification methods according to the sequence of PRDX6. Then the homologous proteins can be obtained by using conventional recombinant methods.

Proteins of the invention may be recombinant polypeptide, natural polypeptide, synthetic polypeptide, and preferably recombinant polypeptide. According to the host used in the recombinant production program, the polypeptides of the present invention may be glycosylated or may be non-glycosylated. Polypeptides of the invention may or may not include a starting methionine residue.

The invention also includes active fragments of human PRDX2 protein, derivatives and analogs thereof. As used herein, the term "active fragment", "derivative" and "analog" refers to a polypeptide of the present invention that substantially remains the same biological function or activity of natural human protein PRDX2. The active fragment, derivative and analog may be (i) polypeptide in which one or more conservative or non-conservative amino acid residue (preferably conserved amino acid residue) are substituted, and such substituted amino acid residue may or may not be encoded by the genetic code, or (ii) polypeptide that having a substituent group in one or more amino acid residues, or (iii) the polypeptide which is formed by the fusion of mature polypeptide with another compound (such as compounds that extend the half-life period of polypeptide, e.g., polyethylene glycol), or (iv) the polypeptide which is formed by fusion of additional amino acid sequence into said polypeptide (such as a leader sequence or secretory sequence or a sequence for purification of said polypeptide, or a proteinogen sequence, or a fusion protein formed thereof with antigen IgG fragment). According to the teachings herein, these fragments, derivatives and analogs are within the knowledge of the skilled in the art.

In the present invention, "human PRDX2 polypeptide" refers to a polypeptide having sequence of SEQ ID NO: 4 and the activity of human protein PRDX2. It also includes the variations of SEQ ID NO: 4 that have same function with human PRDX2 protein. Those variations comprise (but are not limited to): several (usually 1-50, preferably 1-30, more preferably 1-20, the most preferably 1-10) deletion, insertion and/or substitution of amino acid, and one or several (usually 20 or less, preferably 10 or less, more preferably 5 or less) amino acids addition on the C-terminus and/or N-terminus. For example, in the present field, the function of protein won't be changed when it is substituted by amino acids of approximate or similar properties. Again for example, in the present field, the function of protein won't be changed when one or several amino acids are added on the C-terminus and/or N-terminus. It also comprises active fragments or active derivatives of human PRDX2 protein. A preferred active fragment is a polypeptide whose amino acid sequence is shown in position 6 to 164 of SEQ ID NO: 4.

Diseases, Aging or Injury Caused by ROS Increase

The PRDX2 and/or PRDX6 of the present invention can be used to treat or prevent the diseases, aging or injury induced by ROS increase, wherein the diseases, aging or injury induced by ROS increase can be any known diseases, aging or injury caused by reactive oxygen increase, and preferably they comprise (but are not limited to): 1. damages, aging or disease resulting from an increase in ROS caused by irradiation or radiation including cosmic radiation, radiation produced by radioactive elements of earth, ultraviolet, X-ray, radiation produced by welding, computers, televisions, mobile phones and other electrical radiation sources or tumor radiotherapy, such as corneal injury, skin damage, tissue damage including damage of various tissues; 2. damage, aging or diseases resulting from ROS increase caused by hyperglycemia (such as diabetes), such as insulin resistance, pancreatic β cell damage, kidney damage, etc.; 3. various damages of tissues caused by smoking, e.g., lung damage (such as bronchitis, pancreas damage, liver damage); 4. various damages of tissue caused by drinking, such as alcoholic liver disease, pancreatic injury; 5. other diseases inducted by ROS increase, e.g., atherosclerosis, hypertension, cancer, osteoarthritis, rheumatoid arthritis, pulmonary fibrosis, epilepsy or neurodegenerative diseases such as Alzheimer's disease, Parkinson's disease; 6. damage resulting from cell cryopreservation-recovery process wherein the cell includes human or animal sperms, eggs, or any other tissue cells; 7. ischemia reperfusion damage including but not limited to ischemia-reperfusion injury during organ transplantation, microcirculation dredge during shock, relief of coronary artery spasm, heart and brain CPR after sudden cardiac arrest, coronary artery bypass, PTCA, post-surgery of revascularization surgery such as thrombolytic therapy, cardiac cardiopulmonary bypass heart surgery, organ transplantation and severed limb transplantation, etc.; 8. aseptic necrosis of caput femoris; 9. bedsores caused by prolonged bed rest; 10. diseases caused by ROS increase or diseases caused by using medicament such as peroxidation injury caused by using chemotherapy medicament, caused from poisoning of organophosphorus pesticides, or caused by taking toxic drugs for suicide, etc.; 11. dermatic issues, including but not limited to wrinkles, marks and burns, etc.; 12. diabetic complications, e.g., pedopathy (gangrene), eye disease, kidney disease, encephalopathy, etc.

Pharmaceutical Composition and Administration Methods

The pharmaceutical composition of the present invention comprises a safety effective amount of PRDX6 protein and/or PRDX2 protein, and pharmacologically acceptable excipient or carrier. As used herein, "safety effective amount" means an amount of protein is effective to significantly improve the state of disease, while not having serious side effects. Generally, the pharmaceutical composition includes 0.1 ng-2000 mg of PRDX6 protein and/or PRDX2 protein per dose, preferably, includes 1-200 mg of PRDX6 protein and/or PRDX2 protein per dose. Preferably, "dose" is a capsule, tablet or a bottle of eye drop.

"Pharmaceutically acceptable carrier" means one or more compatible solid or liquid filler material or gel, which is suitable for human use, while having enough purity and sufficiently low toxicity. "Compatible" means each component of the composition can be mixed with protein of the present invention, while not reducing the efficacy of the composition. Some of pharmaceutically acceptable carriers are cellulose and its derivatives (such as sodium carboxymethyl cellulose, sodium ethyl cellulose, cellulose acetate, etc.), gelatin, talc, solid lubricant (such as stearic acid, magnesium stearate), calcium sulphate, vegetable oils (such as soybean oil, sesame oil, peanut oil, olive oil, etc.), polyols (such as propylene glycol, glycerol, mannitol, sorbitol and the like), emulsifiers (such as Tween®), wetting agents (eg sodium lauryl sulfate), coloring agents, flavoring agents, stabilizers, antioxidants, preservatives, pyrogen-free water, etc.

There are no particularly limitation on administration methods of PRDX6 protein and/or PRDX2 protein or pharmaceutical composition thereof. The exemplary administration methods include (but are not limited to): oral, rectal, parenteral (intravenous, intramuscular or subcutaneous), and topical administration (such as patches).

Solid dosage forms for oral administration include capsules, tablets, pills, powders, and granules. In those solid dosage forms, the active ingredient is mixed with at least one conventional inert excipients (or carriers), such as sodium citrate or dicalcium phosphate, or mixed with the following ingredients: (a) fillers or compatibilizers, such as starch, lactose, sucrose, and silicate; (b) binders, e.g., hydroxymethyl cellulose, polyvinyl pyrrolidone, sucrose, and acacia; (c) humectants, for example, glycerol; (d) disintegrants such as agar, potato starch or tapioca starch, alginic acid, certain complex silicates, and sodium carbonate; (e) sustained releasing agents, such as paraffin; (f) absorption accelerators, such as quaternary ammonium compounds; (g) wetting agents, such as cetyl alcohol and glycerol monostearate; (h) adsorbents, e.g. kaolin; and (i) lubricants, e.g., talc, calcium stearate, magnesium stearate, solid polyethylene glycols, sodium lauryl sulfate, or a combination thereof. The dosage form of capsules, tablets and pills may also comprise buffering agents.

Solid dosage forms such as tablets, candy, capsules, pills, and granules can be prepared with coatings and shell materials, such as casings and other materials known in the art. They may contain opacifying agents, and the active ingredient of such compositions can be released in a sustained manner in a certain part of the digestive tract. Examples of embedding compositions that can be employed are polymeric substances and waxes substances. When necessary, the above active ingredients may also form a micro-encapsulated form with one or more excipients listed above.

Liquid dosage forms for oral administration include pharmaceutically acceptable emulsions, solutions, suspensions, syrups or tinctures. Apart from the active ingredient, the liquid dosage forms may contain inert diluents conventionally used in the art, such as water or other solvents, solubilizers and emulsifiers, for example, ethanol, isopropyl alcohol, ethyl carbonate, ethyl acetate, propanediol, 1,3-butylene glycol, dimethylformamide and oils, especially cottonseed oil, peanut oil, corn germ oil, olive oil, castor oil and sesame oil, or the mixtures thereof.

In addition to such inert diluents, the composition can also contain auxiliary additives such as wetting agents, emulsifying agents and suspending agents, sweetening agents, flavorings and spices.

In addition to active ingredient, the suspensions may contain suspending agents, for example, ethoxylated isostearyl alcohols, polyoxyethylene sorbitol and sorbitan esters, microcrystalline cellulose, methanol aluminum, agar or the mixtures thereof.

The composition for parenteral injection may comprise physiologically acceptable sterile aqueous or non-aqueous solutions, dispersions, suspensions or emulsions, and sterile powders which can be re-dissolved into sterile injectable solutions or dispersions. Suitable aqueous and nonaqueous carriers, diluents, solvents and excipients include water, ethanol, polyols and any appropriate mixture thereof.

Dosage forms of PRDX6 protein and/or PRDX2 protein for topical administration include ointments, powders, patches, sprays, suppositories, and inhalants. Active ingredient is mixed under sterile conditions with a physiologically acceptable carrier and any preservative, buffer, or propellant when it is necessary.

The protein of the present invention can be administrated individually, or be administrated in the mixture with other pharmaceutically acceptable compounds or protein.

When using the pharmaceutical composition, a safely effective amount of active ingredient is applied to a mammal (e.g., human) in need of treatment, wherein the administered dose is a dose considered as pharmaceutically effective. Daily administrate dose to a 60 kg person is usually 0.5 ng~2000 mg, preferably 2~50 mg. Of course, the specific dose is related to factors such as the route of administration, the patient's health status, which are within the knowledge scope of skilled physicians.

Preferably, the present invention provided a pharmaceutical composition which comprises a safely effective amount of PRDX6 protein and/or PRDX2 protein of the present invention, and pharmaceutically acceptable carriers or excipients. Those carriers or excipients comprise (but are not limited to): saline, buffer, glucose, water, glycerol, ethanol, poloxamer, carbomer, or the combination thereof. For example, the protein of the present invention may be formulated in a non-toxic, inert, pharmaceutically acceptable aqueous carrier medium, wherein the pH is usually about 5-8, preferably the pH is about 6-8, most preferably the pH is about 6.8-7.6, although the pH value can be varied according to the property of the substance to be prepared and the disease to be treated.

The prepared composition can be administered by conventional routes, including (but not limited to) topical, oral, intramuscular, and intravenous administration or subconjunctival injection, etc.

The dosage form should match with administration method. (1) The pharmaceutical compositions of the invention can be made into injections, e.g., prepared by conventional method with saline or aqueous solution containing glucose and other auxiliary agents. (2) Pharmaceutical compositions such as ointments, drops, sprays, capsules, tablets and the like can be prepared by conventional methods. (3) Pharmaceutical compositions such as injections, solutions, tablets and capsules, which should be manufactured under sterile conditions. (4) A suppository can be made, e.g., according to the following specific process: 1. mixing appropriate amount of ethanol with β-CD into a paste, and adding PRDX6, PRDX2 protein and grinding to form inclusion for 45 minutes for further use. 2 dissolving semi-synthetic fatty acid enzyme (type 36) by heating and maintaining at 38° C., and adding inclusion of main active ingredient, fully mixing while the temperature is maintained. 3. The homogenous mixture is poured and shaped by cooling. 4. The prepared suppositories should be placed in the female genital tract before sexual intercourse, thus improving the success rate of pregnancy of asthenospermia patients.

The dosage of the active ingredient is a therapeutically effective amount, e.g., about 1 μg/kg body weight to about 10 mg/kg body weight per day. The pharmaceutical composition of the present invention may also be prepared into eye drops, eye ointment, or gel, preferably under sterile conditions. The amount of active ingredient administered is a therapeutically effective amount, e.g., about 10 μg/kg body weight to about 10 mg/kg body weight per day. Of course, the specific dose is related to factors such as the route of administration, the patient's health status, which are within the knowledge scope of skilled physicians.

Cell Cryoprotectant of the Present Invention

In a preferred embodiment, the present invention provides a formulation of sperms cryoprotectant, which comprises 0.1 mg/ml-100 mg/ml of recombinant PRDX6 protein and/or PRDX2 protein; and some common components for sperm cryoprotectant, e.g., potassium chloride, sodium chloride, magnesium sulfate, sodium dihydrogen phosphate, sodium bicarbonate, glucose, egg yolk, albumin, glycine, sucrose, glycerol.

In addition, PRDX2 protein and PRDX6 protein can be administrated individually, or be administrated together. Moreover, the protein of the present invention can be used with other sperm cryoprotectant.

Treatment of Asthenozoospermia

In a preferred embodiment, the present invention provides a pharmaceutical composition for treatment of asthenospermia, which comprises 1-100 mg active ingredients which is recombinant PRDX2 protein and/or PRDX6 protein; and pharmaceutically acceptable carriers or excipients. Such carriers include (but are not limited to) saline, buffered, dextrose, water, glycerol, Tween 80, β-CD, and combinations thereof.

In addition, PRDX2 protein and PRDX6 protein can be administrated individually, or in combination. Moreover, the protein of the present invention can be used together with other therapeutic agents of asthenospermia.

For example, the function of pharmaceutical composition of the present invention comprises (but not limited to): (1) improving the impregnation rate of asthenospermia patients; (2) protecting spermatids in mature stage.

Treatment of Corneal Injury

In a preferred embodiment, the present invention provides a pharmaceutical composition for treatment of corneal injury. It comprises dripping or applying the protein of the present invention into conjunctival sac directly in a dosage of 0.05-0.2 mg each time. In addition, PRDX2 protein and PRDX6 protein can be administrated individually, or be administrated together. Moreover, the protein of the present invention can be used with other therapeutic agents of corneal injury.

In particular, the pharmaceutical composition have one or more of the following functions: (1) relieving asthenopia, enhancing and improving vision or preventing progressive vision loss; (2) resisting light injuries and lipid peroxidation damages, increasing cellular potential for scavenging oxygen radicals, lowering hue differences, effectively treating myopia, amblyopia, presbyopia, glaucoma, or floaters; (3) inhibiting free radical generation in the vitreous, accelerating clearance and excretion of free radicals, preventing glycation and oxidation of proteins in the vitreous body, protecting SH groups of soluble proteins from damages, restoring insoluble proteins into soluble proteins, preventing phacoscotasmus, or controlling formation and development of progressive cataracts, thereby effectively treating senile cataract, diabetic cataract, traumatic cataract, radiation cataract, after-cataract, or treating phacoscotasmus in immature stage, expansion stage and mature stage.

Treatment of Burn and Scald

In a preferred embodiment, the present invention provides a pharmaceutical composition for treatment of burn and scald. One can apply the protein of the present invention onto the surface of burn and scald in amount of 0.1-0.5 mg/cm$^2$ wound surface. In addition, PRDX2 protein and PRDX6 protein can be administrated individually, or be administrated together. Moreover, the protein of the present invention can be used with other therapeutic agents of burn and scald.

Cosmetic Composition

The present invention provides a cosmetic composition, which comprises PRDX2 protein and/or PRDX6 protein as active ingredients. The composition comprises an effective amount of PRDX2 protein and/or PRDX6 protein, and cosmetically acceptable carriers or excipients.

The cosmetic composition which comprises PRDX2 protein and/or PRDX6 protein as active ingredients of the present invention, may comprise any amount of PRDX2 protein and/or PRDX6 protein appropriate for cosmetic formulation. Generally, the content of PRDX2 protein and/or PRDX6 protein can be 0.1~30%, preferably 1~15%, more preferably 3~8% of the total weight of cosmetic composition.

In the invention, the carriers and excipients for production of cosmetic formulations can be any conventional carriers or excipients known to a person skilled in the art. The selection of a particular carrier or excipient depends on the type of cosmetics to be prepared.

The cosmetic composition of the present invention can be prepared by the methods known to the skilled in the art. For example, PRDX2 protein and/or PRDX6 protein can be blended in any type (oil-in-water and/or oil-in-water type) of cream cosmetics (such as cream, moisturizer, balm, cold cream, foundation), cosmetics (such as lipstick, rouge, eyebrow pencil, eye shadow powder, mascara, eyeliner, nail polish, mask, etc.), powder cosmetics (such as face powder, pressed powder, talcum powder), perfume cosmetics (such as perfume, cologne, floral perfume, quinine water, conditioner, lotion, after-shave, etc.), curative cosmetics (such as skin care agents (traditional Chinese therapy), anti-acne cosmetics, anti-freckle cosmetics, anti-wrinkle and anti-aging cosmetics, slimming cosmetics, whitening cosmetics), sunscreen cosmetics, shaving cream, etc. by using methods known to the skilled in the art.

The cosmetic composition of the present invention has an anti-aging, scar-repairing, anti-wrinkle, wrinkle-erasing, freckle-erasing, whitening, sunscreening, or skin cancer preventing effect. The present invention also relates to the use of the composition in general skin conditioning, in the cosmetic treatment of particular wrinkles, marks and burn.

The main merit of the present invention is that the human PRDX2 protein and/or PRDX6 protein have the following effects:

(1) Protecting the sperms during the process of freezing and reviving sperms. For example, the sperm recovery rate and sperm penetration rate (SPA) is significantly improved when recombinant human PRDX2 protein and/or PRDX6 protein are added into traditional cryoprotectant; (2) Improving quality of the sperms in asthenozoospermia patients. For example, the total number of active sperms is raised and the quality of sperms and the impregnation rate are significantly improved after recombinant human PRDX2 protein and/or PRDX6 protein are added during in vitro treatment of sperm in assisted reproductive technology. (3) Various effects such as anti-aging, repairing scars, preventing wrinkle, erasing wrinkles, erasing freckles, whitening, sunscreening, preventing skin cancer; (4) Treating burn, scald and corneal injuries; (5) Promoting the healing of wounds; (6) Protecting tissues and cells from oxidative damage.

The present invention will be further illustrated below with reference to the specific examples. It should be understood that these examples are only to illustrate the invention but not to limit the scope of the invention. The experimental methods with no specific conditions described in the following examples are generally performed under the conventional conditions, e.g., in the conditions described in Sambrook et al, Molecular Cloning: A Laboratory Manual (New York: Cold Spring Harbor Laboratory Press, 1989), or according to the manufacture's instructions. Unless indicated otherwise, parts and percentage are calculated by weight. The starting materials or reagents used in the invention are commercially available.

Example 1

Construction of Expression Vector pET32b(+)/PRDX6 and pET32b (+)/PRDX2

1.1 Construction of Expression Vector pET32b(+)/PRDX6

A pair of specific primers were designed and synthesized based on the gene sequence encoding mature protein PRDX6,

```
Upstream primer:
                            (as shown in SEQ ID NO: 5);
5'-tatccatatgcccggaggtctgcttc-3'

Downstream primer:
                            (as shown in SEQ ID NO: 6);
5'-ttactcgagaggctggggtgtgtagcg-3'
```

Enzyme site was NdeI and XhoI, respectively.

Figure 1:
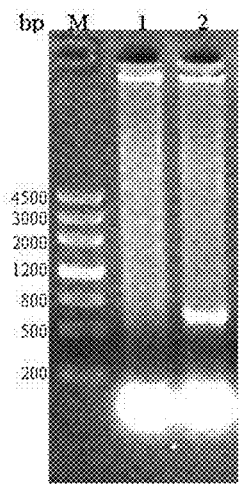

RT-PCR amplification was carried out by using a human epididymis mRNA extracted by conventional method (or a human epididymis cDNA library prepared in laboratory) as a template. The results were shown in FIG. 1. A 688 bp amplified fragment was detected, which was consistent with the theoretical length.

The amplified fragment was separated (Targeted fragment was recovered from agarose gels with gel extraction kit), and was digested with two enzymes NdeI and XhoI. Then, the digested fragment from enzyme digestion was linked into expression vector pET32b (+) (commercially available from Novagen) which was digested into linear form with NdeI and XhoI. Then, the vector was transformed into conventional E. coli TOP10F' (commercially available from Invitrogen). Positive clones were screened by PCR amplification of colony, and then sequenced so as to further confirm the correctness of the sequence and the expression of reading frame, thereby obtaining recombinant expression plasmid pET32b (+)/PRDX6.

PRDX6 protein expressed by the expression vector was PRDX6-His fusion protein, wherein eight amino acids LEH-HHHHH were added onto C-terminal to facilitate separation and purification.

1.2 Construction of Expression Vector pET32b(+)/PRDX2

The construction method was similar to 1.1, wherein the difference was that the following pair of primers were used:

```
Upstream primer:
                            (as shown in SEQ ID NO: 7);
5'-TATCCATATGGCCTCCGGTAACGCGC-3'

Downstream primer:
                            (as shown in SEQ ID NO: 8);
5'-TTACTCGAGATTGTGTTTGGAGAAATATTC-3'
```

Enzyme digestion site was NdeI and XhoI, respectively. The recombinant expression plasmid pET32b(+)/PRDX2 was obtained.

Example 2

Expression of Protein PRDX6 and Protein PRDX2

2.1 Expression of Protein PRDX6

Plasmid pET32b (+)/PRDX6 was used to transform E. coli Origami B (DE3) (purchased from Novagen). The positive clones were inoculated into LB medium containing 100 ug/ml of ampicillin, and cultured with shaking overnight at 37° C.

It was transferred to LB medium containing 100 ug/ml of ampicillin (1:100) on the next day, and was cultured with shaking at 37° C. After the bacterial density reached $OD_{600}$=0.6~0.8, IPTG was added to a final concentration of 0.4 mM to induce the expression of the targeted protein PRDX6. After 3-4 hrs, the bacteria were collected by centrifugation.

2.2 Expression of Protein PRDX2

The expression of protein PRDX2 was conducted using the same method in 2.1, wherein the difference was that protein PRDX2 was used to replace protein PRDX6.

Example 3

Purification of Protein PRDX6 and Protein PRDX2

3.1 Purification of Protein PRDX6

The bacteria collected by centrifugation were re-suspended in buffer A (20 mM phosphate buffer, 150 mM NaCl, pH7.2), and disrupted with ultrasonic in an ice bath, and then centrifuged in low temperature (4° C.) at 20000 g for 15 min. The supernatant was taken as samples to be purified.

Figure 2:
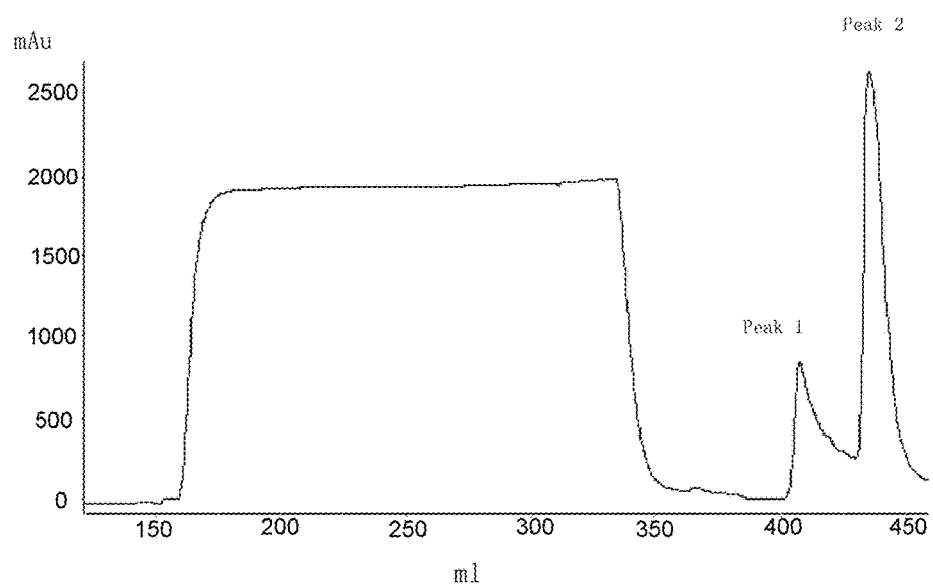

After the nickel affinity column was equilibrated with buffer A, the sample was added onto the column. Then buffer A containing 50 mM imidazole was used to wash column to remove impurity proteins (peak 1) (see FIG. 2). The targeted protein was eluted with buffer A containing 300 mM imidazole (peak 2) (see FIG. 2).

Finally, the eluted protein was transferred to buffer A by using G-25 desalting column to remove imidazole, and detected by SDS-PAGE electrophoresis.

Figure 3:
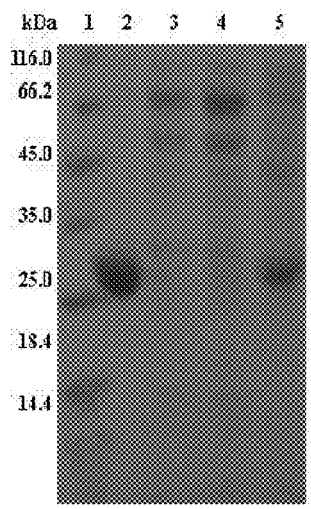

After analyzing, the purity of obtained protein PRDX6 was more than 95% and the molecular weight was about 26.1 kD. (See FIG. 3)

3.2 Purification of Protein PRDX2

Protein PRDX2 was purified using the same method of 3.1, wherein the difference was that the protein PRDX2 was used to replace protein PRDX6.

Example 4

The Antioxidant Activity of Protein PRDX6 (Oxidative Damage Experiment of HEF Cells)

The HEF cells were common human embryonic fibroblasts (Zavada et. al., Nature New Biology, 240: 124-125 (1972); or U.S. Pat. No. 7,811,817).

The cells were revived with culture medium (high glucose DMEM +5% FBS, purchased from Invitrogen), and cultured for 48 h.

When the cells grew to 90% confluence, PRDX6 protein (PRDX6-His fusion protein) obtained in Example 3 was added into the culture system in accordance with the following experimental method, and then $H_2O_2$ was added. After 30 min, cell viability was detected by MTT method.

Design of Experiment:

Factor 1: $H_2O_2$ level (1 mM, 0.5 mM, 0.25 mM, 0.125 mM, and 0 mM)

Factor 2: PRDX6-His level (0.5 mg/ml, 0.25 mg/ml, 0.125 mg/ml, and 0 mg/ml)

The concentration of $H_2O_2$ and PRDX6-His of each experimental group is shown in Table 1.

TABLE 1

| $H_2O_2$ (mM) | PRDX6-His (mg/ml) | Mean of $OD_{490}$ | cell mortality rate (%) | cell survival rate (%) |
|---|---|---|---|---|
| 1 | 0.5 | 0.0037 | 99.18 | — |
|  | 0.25 | 0.0023 | 99.48 | — |
|  | 0.125 | 0.007 | 98.43 | — |
|  | 0 | 0.0147 | 96.71 | — |
| 0.5 | 0.5 | 0.014 | 96.86 | 3.14 |
|  | 0.25 | 0.008 | 98.20 | 2.90 |
|  | 0.125 | 0.0127 | 97.16 | 2.84 |
|  | 0 | 0.0023 | 99.48 | 0.52 |
| 0.25 | 0.5 | 0.1993 | 55.27 | 44.73 |
|  | 0.25 | 0.085 | 80.93 | 19.07 |
|  | 0.125 | 0.006 | 98.65 | 1.35 |
|  | 0 | 0.0143 | 96.78 | 3.22 |
| 0.125 | 0.5 | 0.292 | 34.48 | 65.52 |
|  | 0.25 | 0.2897 | 35.00 | 65.00 |
|  | 0.125 | 0.0123 | 97.23 | 2.77 |
|  | 0 | 0.011 | 97.53 | 2.47 |
| 0 | 0.5 | 0.4987 | −11.89 | 111.89 |
|  | 0.25 | 0.4753 | −6.66 | 106.66 |
|  | 0.125 | 0.444 | 0.37 | 99.63 |
|  | 0 | 0.4457 | 0 | 100 |

Figure 4:
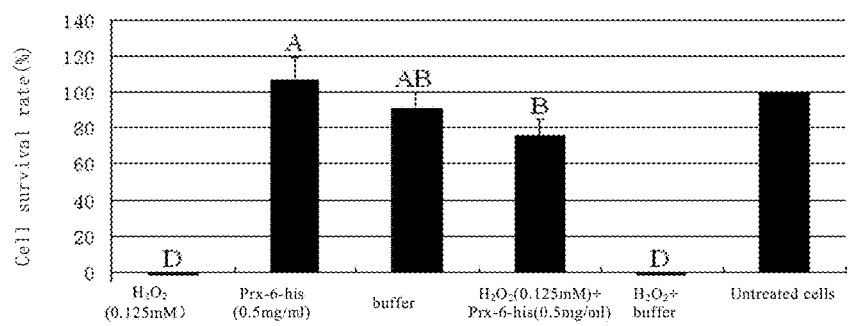
FIG. 4 shows the protective effect of recombinant PRDX6 protein on HEF cells against oxidation (P<0.05).

The results were shown in Table 1 and FIG. 4.

$H_2O_2$ group (0.125 mM): $H_2O_2$ had strong toxic effect on cells. The survival rate of cells was only 2.47% when the concentration of $H_2O_2$ was 0.125 mM. The resulting harm was more severe when the concentration of $H_2O_2$ was raised.

The buffer group (20 mM phosphate buffer, 150 mM NaCl, pH7.2, containing 0.5 mg/ml of 6× His expression tag): When only said buffer was existed, the survival rate was remarkably reduced when compared with the protein PRDX6-His (0.5 mg/ml) group.

$H_2O_2$+PRDX6-His group: Taking each group as an example wherein the concentration of $H_2O_2$ was 0.125 mM, protein PRDX6 (0.25 mg/ml, and 0.5 mg/ml) was added, respectively. Among them, 0.25 mg/ml protein could make HEF cells resist the harm caused by 0.125 mM $H_2O_2$ to a certain extent; and 0.5 mg/ml PRDX6 could significantly increase the survival rate from about 2.5% to 65%.

$H_2O_2$+buffer (the same as the former) group: It was indicated that the buffer containing 6× His expression tag could not play a protective role.

The above results show that the survival rate of cells can be remarkably increased when protein PRDX6-His existed in the system. The protein PRDX6-His could resist the peroxidation damage from $H_2O_2$.

Example 5

The Protection of Protein PRDX2 and Protein PRDX6 on Sperm in Asthenozoospermia Patients Steps:

1. The sperm samples were taken, the progressive motility rate of sperm (PR) % was detected after liquefaction, and the sperm samples with (PR) % less than 32% (asthenozoospermia) were chosen.

2. Floating in BWW culture solution for 1 h.

3. Sperms were washed with BWW culture solution for 3 times.

4. Said sperms were divided into three groups:

blank control group (sperms were diluted in BWW+buffer (20 mM phosphate buffer, 150 mM NaCl, pH7.2));

BSA group (sperms were diluted in BWW+300 ug/ml bovine serum albumin (BSA, purchased from Amresco)); and protein group (sperms were diluted in BWW+300 ug/ml protein).

5. Sperm motion parameters were detected after incubated for 2 h and 4 h, respectively.

Figure 5:
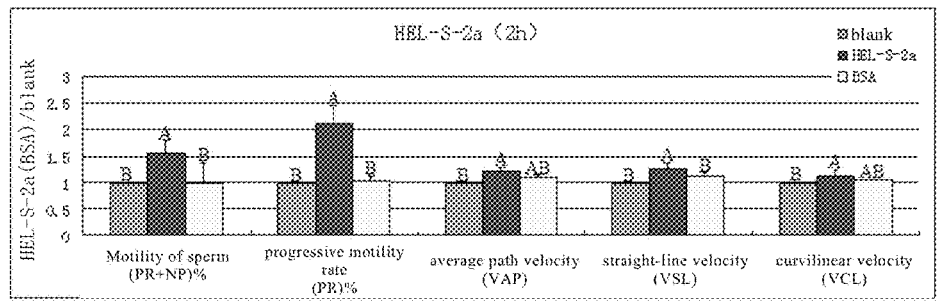
FIG. 5 shows the protective effect of PRDX2 protein (i.e., HEL-S-2a) on weak sperms.

Results:

(1) For the sperm samples whose the progressive motility rate of sperm (PR) % was less than 32%, after 2 h incubation, the motility rate, progressive motility rate of sperm, average path velocity, straight-line velocity and the curvilinear velocity of sperms in HEL-S-2a protein (i.e., protein PRDX2) group were significantly higher than those in the control group. The motility rate, progressive motility rate of sperm and straight-line velocity of sperms in HEL-S-2a protein group were significantly higher than those in the BSA group. The results of statistical analysis were shown in FIG. 5.

Figure 6:
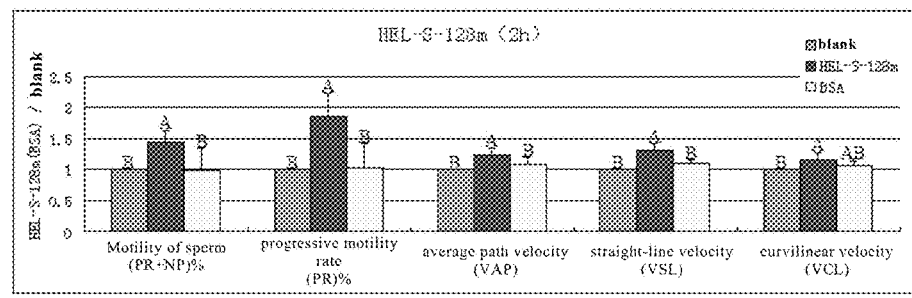
FIG. 6 shows the protective effect of PRDX6 protein (i.e., HEL-S-128m) on weak sperms.

(2) For the sperm samples whose the progressive motility rate of sperm (PR) % was less than 32%, after 2 h incubation, the motility rate, progressive motility rate of sperm, average path velocity, straight-line velocity and the curvilinear velocity of sperms in HEL-S-128m protein (i.e., protein PRDX6) group were significantly higher than those in the control group. The motility rate, movement sperms' percentage, average path velocity and straight-line velocity of sperms in HEL-S-128m protein group were significantly higher than those in the BSA group. The results of statistical analysis were shown in FIG. 6.

In the sperm treating process of in vitro assisting reproductive technology, adding recombinant human PRDX2 protein and PRDX6 protein of the present invention can increase the number of motile treated sperms, and improve the quality of the treated sperms, thus improving the impregnation rate.

Example 6

Prescription of Suppositories for the Treatment of Infertility and the Preparation Method

TABLE 2 the ingredients for the preparation of suppository and the dosage thereof

| Ingredient | dosage |
|---|---|
| Protein PRDX2 | 5 mg |
| Protein PRDX6 | 5 mg |
| β-CD | 10 mg |
| Tween 80 | 2 mg |
| semi-synthetic fatty acid enzyme (type 36) | 40 mg |

Preparation process of suppository, the ingredients and the dosage thereof were shown in Table 2:

1. Appropriate amount of ethanol was added into β-CD under stirring, thereby forming a paste, and protein was added and grinded to form inclusion for 45 minutes for further use.
2. Semi-synthetic fatty acid enzyme (Type 36) was dissolved by heating and maintaining at 38° C., the inclusion of main active ingredient was added, fully mixed while the temperature was maintained.
3. The homogenous mixture was poured and cooled to form into film.

Example 7

Prescription of Sperm Cryoprotectants and Protective Effect Thereof 7.1 Prescription of Sperm Cryoprotectants In every 100 ml of sperm cryoprotectant, there were: protein PRDX6 500 mg, protein PRDX2 500 mg, KCl 0.54 mmol/L, NaCl 10.0 mmol/L, MgSO$_4$ 0.05 mmol/L, NaH$_2$PO$_4$ 0.03 mmol/L, NaHCO$_3$ 10 mmol/L, glucose 205.4 mmol/L, glycine 13.0 mmol/L, sucrose 5.0 mmol/L, HEPES 2.5 mmol/L, glycerol 14% (v/v).

The basic formulation was formulated with double-distilled water, adjusted pH to 7.4, and filtered to remove bacteria with 0.22 um sterile filter.

7.2 Comparison the Protective Effect of Sperm Cryoprotectants of the Present Invention with that of Commercial Products 7.2.1 Materials Sperm samples were donated by 20 healthy, married 30 to 35 years old volunteers having children. The volunteers were involved in the present study after detection of urology and normal sperm inspection.

7.2.2 Methods

More than 2 ml sperm was collected from each volunteer, and was divided into 3 parts.

One of them was for pre-frozen normal sperm inspection and SPA determination;

The remaining 2 parts were frozen with the cryoprotectant of Example 7 of the present invention and the commercial product, respectively, and warmed after 6 months. The normal sperm inspection and SPA determination were conducted.

7.2.3 The Results were Shown in Table 3.

TABLE 3

| Group | Number of copies | Sperm motility rate (%) | Recovery rate (%) | SPA (%) |
|---|---|---|---|---|
| Pre-frozen group | 20 | 73.7 ± 3.4 | | 41.5 ± 4.1 |
| Cryoprotectant of the present invention group | 20 | 61.4 ± 2.7 | 81.2 ± 2.5 | 28.9 ± 3.5 |
| Commercial cryoprotectant group | 20 | 52.3 ± 3.6 | 70.2 ± 3.1 | 21.2 ± 3.2 |

Cryoprotectant of the present invention was considerably superior to the commercial cryoprotectant in sperm recovery rate and sperm penetration rate (SPA) ($P<0.01$).

Example 8

The Therapeutical Effect of Active Fragments

The Example 5 and 7 were repeated, wherein the difference was that the Prx-6 active fragment as shown in position 5 to 169 of SEQ ID NO: 2 was used to replace the whole length Prx-6 protein shown in SEQ ID NO: 2, and the Prx-2 active fragment as shown in position 6 to 164 of SEQ ID NO: 4 was used to replace the whole length Prx-2 protein shown in SEQ ID NO: 4.

The results showed that the above fragments had a protective effect on sperms in asthenozoospermia patients, and could significantly improve the quality of the treated sperms, thereby improving the impregnation rate, the therapeutical effect was equivalent to that of the whole length Prx-6 and Prx-2. The above fragments could also serve as sperm cryoprotectant and considerably improve sperm recovery rate and sperm penetration rate.

Example 9

Therapeutical Effect of Protein Prx-6 on Corneal Injury 9.1 Animal Source: 6-week-aged SD rats purchased from Experimental Animal Center of Yantai Yuhuangding Hospital.

9.2 medicaments: Experimental group: protein Prx-6 prepared in Example 3; control group: normal saline.

9.3 Preparation of Corneal Injury Model

5% chloral hydrate (7 ml/kg body weight) was injected into enterocoelia. Tropicamidum and Neosynephrine eye drops were used as mydriatic after anesthesia once every 2 min, and 1 drop every time. After 20 min, mydriatic agent on cornea and conjunctiva was sucked carefully with a cotton swab after mydriasis. The rat was placed under 300 nm UV lamp, and fixed according to the relative position height of UV lamp, and irradiance was measured with UV radiation detector, controlled at $1\times10^3$ Uw/cm$^2$. The total daily radiation dose was 9 KJ/m$^2$, for 3 consecutive days, so that corneal injury model in rats was prepared. And slit lamp microscope was used to observe.

9.4 Treatment Method

The experiments comprised a control group (dripped with normal saline), Prx-6 protein treatment group (dropped with 2 mg/ml Prx-6 protein). Two days after corneal injury, the administration was started, 4 times a day and 2 drops (approximately 30 μl) were dripped into rat's ocular every time.

9.5 Experimental Result

Two days after UV irradiation, there was edema on rat corneal and transparency was decreased obviously. On the 4th day of treatment, there was more neovascularization in corneal in the control group and there was strong inflammatory response, while there was little neovascularization in corneal in the Prx-6 protein treatment group and the edema was reduced significantly; on the 8th day of treatment, the edema in corneal of the control group was reduced slightly and transparency partially recovered, while corneal transparency of the Prx-6 protein treatment group mostly recovered; on the 12th day of treatment, the corneal transparency in the control group was not fully recovered, while corneal of rat in the Prx-6 protein treatment group was almost recovered, and edema was eliminated (FIG. 7). (Note: from left to right the figure: control group (2 rats); Prx-6 treatment group (2 rats)).

Example 10

The Activity Assay of PRDX2 and PRDX6

Hydrogen peroxide had strong absorption at wavelength 240 nm, which was proportional to the concentration (A240 nm×22.94=the concentration of hydrogen peroxide mM). Both PRDX6 and PRDX2 were capable of decomposing hydrogen peroxide so that the absorbance (A240 nm) of reaction solution was reduced over the reaction time.

Experimental protocol: 10 mM hydrogen peroxide was prepared with buffer (20 mM phosphate buffer, 150 mM NaCl, pH7.2). 500 ul was taken, and 10 ul of the protein (quantitated by BCA method) was added, and reacted at 25° C. for 20 min. The amount of consumed hydrogen peroxide was calculated by measuring the absorbance difference between before and after the reaction, so as to calculate the amount of hydrogen peroxide (nmol) consumed by per ug protein in 1 min, i.e. nmol/min/ug, thus evaluating the activity of PRDX6 or PRDX2.

Experimental results of PRDX6 were shown in Table 4, and the results showed that the activity of PRDX6 of the present invention reached to more than 1 nmol/min/ug.

TABLE 4

| Batch number | concentration of protein | Before reaction $A_{240\,nm}$ | After reaction $A_{240\,nm}$ | difference value | activity nmol/min/ug |
|---|---|---|---|---|---|
| 20110901 | 3.0 mg/ml | 0.4145 | 0.2389 | 0.1756 | 3.42 |
| 20110902 | 3.2 mg/ml | 0.3996 | 0.2288 | 0.1708 | 3.12 |
| 20110903 | 3.5 mg/ml | 0.3928 | 0.2271 | 0.1657 | 2.77 |

The results of PRDX6 also showed that the activity of PRDX2 could reach to more than 1 nmol/min/ug.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

The invention claimed is:

1. A method for improving sperm quality or treatment of male infertility, which comprises administrating (i) PRDX2 protein, or (ii) a composition comprising (a) PRDX2 protein and (b) a pharmaceutically acceptable carrier to an asthenospermia patient,
wherein the PRDX2 protein comprises the amino acid sequence of SEQ ID NO: 4, or the amino acid sequence from position 6 to 164 of SEQ ID NO: 4, or a fusion protein thereof formed with an His expression tag.

2. The method of claim 1, which further comprises administrating PRDX6 protein, or a composition comprising (a) PRDX6 protein and (b) a pharmaceutically acceptable carrier to the asthenospermia patient,
wherein the PRDX6 protein comprises the amino acid sequence of SEQ ID NO:2, or the amino acid sequence from position 5 to 169 of SEQ ID NO: 2, or a fusion protein thereof formed with an His expression tag.

3. The method of claim 1, wherein the PRDX2 protein is the protein defined by the amino acid sequence of SEQ ID NO: 4, or the protein defined by the amino acid sequence from position 6 to 164 of SEQ ID NO: 4, or the fusion protein thereof formed with an His expression tag.

4. The method of claim 1, wherein the PRDX2 protein is the protein defined by the amino acid sequence of SEQ ID NO: 4, or the protein defined by the amino acid sequence from position 6 to 164 of SEQ ID NO: 4.

5. The method of claim 1, wherein the PRDX2 protein is the protein defined by the amino acid sequence of SEQ ID NO: 4.

6. The method of claim 2, wherein the PRDX6 protein is the protein defined by the amino acid sequence of SEQ ID NO: 2, or the protein defined by the amino acid sequence from position 5 to 169 of SEQ ID NO: 2, or the fusion protein thereof formed with an His expression tag.

7. The method of claim 2, wherein the PRDX6 protein is the protein defined by the amino acid sequence of SEQ ID NO: 2, or the protein defined by the amino acid sequence from position 5 to 169 of SEQ ID NO: 2.

8. The method of claim 2, wherein the PRDX6 protein is the protein defined by the amino acid sequence of SEQ ID NO: 2.

9. The method of claim 1, wherein the composition is a sperm cryoprotectant.

10. The method of claim 9, wherein 100 ml of sperm cryoprotectant comprises: PRDX6 protein 500 mg; PRDX2 protein 500 mg; KCl 0.54 mmol/L; NaCl 10.0 mmol/L; $MgSO_4$ 0.05 mmol/L; $NaH_2PO_4$ 0.03 mmol/L; $NaHCO_3$ 10 mmol/L; glucose 205.4 mmol/L; glycine 13.0 mmol/L; sucrose 5.0 mmol/L; HEPES 2.5 mmol/L; glycerol 14% (v/v), and the sperm cryoprotectant is formulated with double-distilled water, adjusted pH to 7.4, and filtered to remove bacteria with 0.22 μm sterile filter.

* * * * *

SEQUENCE LISTING

```
<160> NUMBER OF SEQ ID NOS: 8

<210> SEQ ID NO 1
<211> LENGTH: 1715
<212> TYPE: DNA
<213> ORGANISM: Homo sapiens
<220> FEATURE:
<221> NAME/KEY: CDS
<222> LOCATION: (52)..(726)

<400> SEQUENCE: 1
gaaccaaccg gttgcttgct gtcccagcgg cgccccctca tcaccgtcgc c atg ccc        57
                                                         Met Pro
                                                          1 gga ggt ctg ctt ctc ggg gac gtg gct ccc aac ttt gag gcc aat acc       105
Gly Gly Leu Leu Leu Gly Asp Val Ala Pro Asn Phe Glu Ala Asn Thr
         5                  10                  15 acc gtc ggc cgc atc cgt ttc cac gac ttt ctg gga gac tca tgg ggc       153
Thr Val Gly Arg Ile Arg Phe His Asp Phe Leu Gly Asp Ser Trp Gly
     20                  25                  30 att ctc ttc tcc cac cct cgg gac ttt acc cca gtg tgc acc aca gag       201
Ile Leu Phe Ser His Pro Arg Asp Phe Thr Pro Val Cys Thr Thr Glu
 35                  40                  45                  50 ctt ggc aga gct gca aag ctg gca cca gaa ttt gcc aag agg aat gtt       249
Leu Gly Arg Ala Ala Lys Leu Ala Pro Glu Phe Ala Lys Arg Asn Val
                 55                  60                  65 aag ttg att gcc ctt tca ata gac agt gtt gag gac cat ctt gcc tgg       297
Lys Leu Ile Ala Leu Ser Ile Asp Ser Val Glu Asp His Leu Ala Trp
             70                  75                  80 agc aag gat atc aat gct tac aat tgt gaa gag ccc aca gaa aag tta       345
```

```
                    Ser Lys Asp Ile Asn Ala Tyr Asn Cys Glu Glu Pro Thr Glu Lys Leu
                            85                  90                  95 cct ttt ccc atc atc gat gat agg aat cgg gag ctt gcc atc ctg ttg         393
Pro Phe Pro Ile Ile Asp Asp Arg Asn Arg Glu Leu Ala Ile Leu Leu
        100                 105                 110 ggc atg ctg gat cca gca gag aag gat gaa aag ggc atg cct gtg aca         441
Gly Met Leu Asp Pro Ala Glu Lys Asp Glu Lys Gly Met Pro Val Thr
115                 120                 125                 130 gct cgt gtg gtg ttt gtt ttt ggt cct gat aag aag ctg aag ctg tct         489
Ala Arg Val Val Phe Val Phe Gly Pro Asp Lys Lys Leu Lys Leu Ser
                135                 140                 145 atc ctc tac cca gct acc act ggc agg aac ttt gat gag att ctc agg         537
Ile Leu Tyr Pro Ala Thr Thr Gly Arg Asn Phe Asp Glu Ile Leu Arg
            150                 155                 160 gta gtc atc tct ctc cag ctg aca gca gaa aaa agg gtt gcc acc cca         585
Val Val Ile Ser Leu Gln Leu Thr Ala Glu Lys Arg Val Ala Thr Pro
        165                 170                 175 gtt gat tgg aag gat ggg gat agt gtg atg gtc ctt cca acc atc cct         633
Val Asp Trp Lys Asp Gly Asp Ser Val Met Val Leu Pro Thr Ile Pro
180                 185                 190 gaa gaa gaa gcc aaa aaa ctt ttc ccg aaa gga gtc ttc acc aaa gag         681
Glu Glu Glu Ala Lys Lys Leu Phe Pro Lys Gly Val Phe Thr Lys Glu
195                 200                 205                 210 ctc cca tct ggc aag aaa tac ctc cgc tac aca ccc cag cct taa             726
Leu Pro Ser Gly Lys Lys Tyr Leu Arg Tyr Thr Pro Gln Pro
                215                 220 gtctcttgga gaagctggtg ctgtgagcca gaggatgtca gctgccaatt gtgttttcct       786
gcagcaattc cataaacaca tcctggtgtc atcacagcca aggttttag gttgctatac        846 caatggctta ttaaatgaaa atggcactaa aagtttcttg agattcttta tactctctgc       906
cttcagcaat caattccatt catacatcag cactctgctg gttctgtttg aaatatgttc       966
tgtatttaaa actcaaatct tgttggatct ctgcagggct tgtgaccaat gaagtcatat      1026
ttgttgatgg ttgacaaagc ttgcttcact ccatcagaga atgactatca attttttttt     1086
aactgtccta tcacgtcctc tcctgtcacc cattttgaag agtggcagaa cttgaagttc      1146
aacttcctct gtaaatatcc aagtataaag cccaggaact tctagaataa cccagatgcg      1206
ctttaatttt ttttaatatg ttttgatcac agaacttcta gaataaccca gatgctcttt      1266
catattcttt taatacatct tgatcacagc tgggggaaaa aaagcttttt aattctatac      1326
cttcctagta gataagtgaa gagcagggaa agagaccttt aaatattttg ctataaaaaa      1386
atttgtgata agtttctatc aaaatgggga gattgcagaa aaggcttccc ttggctccca      1446
aggaggtgta gcaggtgtga gcaatattag tgccatgtgc ctttcacaca gggtttgcat      1506
ttatcagtct gttttccgat gatgtgtaca tgaaagagta caccatgtga agagaagaga      1566
gaatgattga aaatgtttta gtatagaact cttcttgcag tgggttgcta ttttctagat      1626
tttacttttt agggaacaaa ataaaatcct tgttaaaac tgggaaaaaa aaaaaaaaa        1686 aaaaaaaaa aaaaaaaaa aaaaaaaa                                           1715

<210> SEQ ID NO 2
<211> LENGTH: 224
<212> TYPE: PRT
<213> ORGANISM: Homo sapiens

<400> SEQUENCE: 2

Met Pro Gly Gly Leu Leu Leu Gly Asp Val Ala Pro Asn Phe Glu Ala
1               5                   10                  15
```

```
Asn Thr Thr Val Gly Arg Ile Arg Phe His Asp Phe Leu Gly Asp Ser
            20                  25                  30

Trp Gly Ile Leu Phe Ser His Pro Arg Asp Phe Thr Pro Val Cys Thr
        35                  40                  45

Thr Glu Leu Gly Arg Ala Ala Lys Leu Ala Pro Glu Phe Ala Lys Arg
    50                  55                  60

Asn Val Lys Leu Ile Ala Leu Ser Ile Asp Ser Val Glu Asp His Leu
65                  70                  75                  80

Ala Trp Ser Lys Asp Ile Asn Ala Tyr Asn Cys Glu Glu Pro Thr Glu
                85                  90                  95

Lys Leu Pro Phe Pro Ile Ile Asp Asp Arg Asn Arg Glu Leu Ala Ile
            100                 105                 110

Leu Leu Gly Met Leu Asp Pro Ala Glu Lys Asp Glu Lys Gly Met Pro
        115                 120                 125

Val Thr Ala Arg Val Val Phe Val Phe Gly Pro Asp Lys Lys Leu Lys
    130                 135                 140

Leu Ser Ile Leu Tyr Pro Ala Thr Thr Gly Arg Asn Phe Asp Glu Ile
145                 150                 155                 160

Leu Arg Val Val Ile Ser Leu Gln Leu Thr Ala Glu Lys Arg Val Ala
                165                 170                 175

Thr Pro Val Asp Trp Lys Asp Gly Asp Ser Val Met Val Leu Pro Thr
            180                 185                 190

Ile Pro Glu Glu Glu Ala Lys Lys Leu Phe Pro Lys Gly Val Phe Thr
        195                 200                 205

Lys Glu Leu Pro Ser Gly Lys Lys Tyr Leu Arg Tyr Thr Pro Gln Pro
    210                 215                 220

<210> SEQ ID NO 3
<211> LENGTH: 597
<212> TYPE: DNA
<213> ORGANISM: homo sapiens
<220> FEATURE:
<221> NAME/KEY: CDS
<222> LOCATION: (1)..(594)

<400> SEQUENCE: 3 atg gcc tcc ggt aac gcg cgc atc gga aag cca gcc cct gac ttc aag      48
Met Ala Ser Gly Asn Ala Arg Ile Gly Lys Pro Ala Pro Asp Phe Lys
1               5                   10                  15 gcc aca gcg gtg gtt gat ggc gcc ttc aaa gag gtg aag ctg tcg gac      96
Ala Thr Ala Val Val Asp Gly Ala Phe Lys Glu Val Lys Leu Ser Asp
            20                  25                  30 tac aaa ggg aag tac gtg gtc ctc ttt ttc tac cct ctg gac ttc act     144
Tyr Lys Gly Lys Tyr Val Val Leu Phe Phe Tyr Pro Leu Asp Phe Thr
        35                  40                  45 ttt gtg tgc ccc acc gag atc atc gcg ttc agc aac cgt gca gag gac     192
Phe Val Cys Pro Thr Glu Ile Ile Ala Phe Ser Asn Arg Ala Glu Asp
    50                  55                  60 ttc cgc aag ctg ggc tgt gaa gtg ctg ggc gtc tcg gtg gac tct cag     240
Phe Arg Lys Leu Gly Cys Glu Val Leu Gly Val Ser Val Asp Ser Gln
65                  70                  75                  80 ttc acc cac ctg gct tgg atc aac acc ccc cgg aaa gag gga ggc ttg     288
Phe Thr His Leu Ala Trp Ile Asn Thr Pro Arg Lys Glu Gly Gly Leu
                85                  90                  95 ggc ccc ctg aac atc ccc ctg ctt gct gac gtg acc aga cgc ttg tct     336
Gly Pro Leu Asn Ile Pro Leu Leu Ala Asp Val Thr Arg Arg Leu Ser
            100                 105                 110
```

```
gag gat tac ggc gtg ctg aaa aca gat gag ggc att gcc tac agg ggc    384
Glu Asp Tyr Gly Val Leu Lys Thr Asp Glu Gly Ile Ala Tyr Arg Gly
        115                 120                 125 ctc ttt atc atc gat ggc aag ggt gtc ctt cgc cag atc act gtt aat    432
Leu Phe Ile Ile Asp Gly Lys Gly Val Leu Arg Gln Ile Thr Val Asn
130                 135                 140 gat ttg cct gtg gga cgc tcc gtg gat gag gct ctg cgg ctg gtc cag    480
Asp Leu Pro Val Gly Arg Ser Val Asp Glu Ala Leu Arg Leu Val Gln
145                 150                 155                 160 gcc ttc cag tac aca gac gag cat ggg gaa gtt tgt ccc gct ggc tgg    528
Ala Phe Gln Tyr Thr Asp Glu His Gly Glu Val Cys Pro Ala Gly Trp
                165                 170                 175 aag cct ggc agt gac acg att aag ccc aac gtg gat gac agc aag gaa    576
Lys Pro Gly Ser Asp Thr Ile Lys Pro Asn Val Asp Asp Ser Lys Glu
            180                 185                 190 tat ttc tcc aaa cac aat tag                                        597
Tyr Phe Ser Lys His Asn
        195

<210> SEQ ID NO 4
<211> LENGTH: 198
<212> TYPE: PRT
<213> ORGANISM: homo sapiens

<400> SEQUENCE: 4

Met Ala Ser Gly Asn Ala Arg Ile Gly Lys Pro Ala Pro Asp Phe Lys
1               5                   10                  15

Ala Thr Ala Val Val Asp Gly Ala Phe Lys Glu Val Lys Leu Ser Asp
            20                  25                  30

Tyr Lys Gly Lys Tyr Val Val Leu Phe Phe Tyr Pro Leu Asp Phe Thr
        35                  40                  45

Phe Val Cys Pro Thr Glu Ile Ile Ala Phe Ser Asn Arg Ala Glu Asp
    50                  55                  60

Phe Arg Lys Leu Gly Cys Glu Val Leu Gly Val Ser Val Asp Ser Gln
65                  70                  75                  80

Phe Thr His Leu Ala Trp Ile Asn Thr Pro Arg Lys Glu Gly Gly Leu
                85                  90                  95

Gly Pro Leu Asn Ile Pro Leu Leu Ala Asp Val Thr Arg Arg Leu Ser
            100                 105                 110

Glu Asp Tyr Gly Val Leu Lys Thr Asp Glu Gly Ile Ala Tyr Arg Gly
        115                 120                 125

Leu Phe Ile Ile Asp Gly Lys Gly Val Leu Arg Gln Ile Thr Val Asn
    130                 135                 140

Asp Leu Pro Val Gly Arg Ser Val Asp Glu Ala Leu Arg Leu Val Gln
145                 150                 155                 160

Ala Phe Gln Tyr Thr Asp Glu His Gly Glu Val Cys Pro Ala Gly Trp
                165                 170                 175

Lys Pro Gly Ser Asp Thr Ile Lys Pro Asn Val Asp Asp Ser Lys Glu
            180                 185                 190

Tyr Phe Ser Lys His Asn
        195

<210> SEQ ID NO 5
<211> LENGTH: 26
<212> TYPE: DNA
<213> ORGANISM: artificial sequence
<220> FEATURE:
<221> NAME/KEY: misc_feature
<223> OTHER INFORMATION: primer
```

```
<400> SEQUENCE: 5
tatccatatg cccggaggtc tgcttc                                    26

<210> SEQ ID NO 6
<211> LENGTH: 27
<212> TYPE: DNA
<213> ORGANISM: artificial sequence
<220> FEATURE:
<221> NAME/KEY: misc_feature
<223> OTHER INFORMATION: primer

<400> SEQUENCE: 6
ttactcgaga ggctggggtg tgtagcg                                   27

<210> SEQ ID NO 7
<211> LENGTH: 26
<212> TYPE: DNA
<213> ORGANISM: artificial sequence
<220> FEATURE:
<221> NAME/KEY: misc_feature
<223> OTHER INFORMATION: primer

<400> SEQUENCE: 7
tatccatatg gcctccggta acgcgc                                    26

<210> SEQ ID NO 8
<211> LENGTH: 30
<212> TYPE: DNA
<213> ORGANISM: artificial sequence
<220> FEATURE:
<221> NAME/KEY: misc_feature
<223> OTHER INFORMATION: primer

<400> SEQUENCE: 8
ttactcgaga ttgtgtttgg agaaatattc                                30
```